US008521289B2

(12) United States Patent
Cazares et al.

(10) Patent No.: US 8,521,289 B2
(45) Date of Patent: *Aug. 27, 2013

(54) AUTOMATED DEVICE PROGRAMMING AT CHANGEOUT

(75) Inventors: Shelley M. Cazares, Washington, DC (US); Dan Li, Shoreview, MN (US); Jonathan Kwok, Holmdel, NJ (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/603,934

(22) Filed: Sep. 5, 2012

(65) Prior Publication Data

US 2012/0330381 A1 Dec. 27, 2012

Related U.S. Application Data

(60) Continuation of application No. 12/839,913, filed on Jul. 20, 2010, now Pat. No. 8,271,088, which is a division of application No. 11/427,407, filed on Jun. 29, 2006, now Pat. No. 7,783,356.

(51) Int. Cl.
*A61N 1/362* (2006.01)

(52) U.S. Cl.
USPC .......................................................... 607/32

(58) Field of Classification Search
USPC .............................................. 607/30–32, 59
See application file for complete search history.

(56) References Cited

U.S. PATENT DOCUMENTS

| | | | |
|---|---|---|---|
| 6,039,251 A | 3/2000 | Holowko et al. | |
| 6,285,909 B1 | 9/2001 | Sweeney et al. | |
| 6,628,985 B2 | 9/2003 | Sweeney et al. | |
| 6,860,896 B2 | 3/2005 | Leber et al. | |
| 8,271,088 B2 | 9/2012 | Cazares et al. | |
| 2005/0182767 A1 | 8/2005 | Shoemaker et al. | |
| 2008/0004500 A1 | 1/2008 | Cazares et al. | |
| 2010/0292761 A1 | 11/2010 | Cazares et al. | |

OTHER PUBLICATIONS

"U.S. Appl. No. 11/427,407, Non-Final Office Action mailed Jul. 15, 2009", 13 pgs.
"U.S. Appl. No. 11/427,407, Notice of Allowance mailed Apr. 20, 2010", 7 pgs.
"U.S. Appl. No. 11/427,407, Response filed May 18, 2009 to Restriction Requirement mailed Apr. 17, 2009", 12 pgs.
"U.S. Appl. No. 11/427,407, Response filed Dec. 4, 2009 to Non Final Office Action mailed Jul. 15, 2009", 6 pgs.
"U.S. Appl. No. 11/427,407, Restriction Requirement mailed Apr. 17, 2009", 16 pgs.
"U.S. Appl. No. 12/839,913, Examiner Interview Summary mailed Mar. 8, 2012", 3 pgs.
"U.S. Appl. No. 12/839,913, Non Final Office Action mailed Nov. 7, 2011", 10 pgs.

(Continued)

*Primary Examiner* — Allen Porter, Jr.
(74) *Attorney, Agent, or Firm* — Schwegman Lundberg & Woessner, P.A.

(57) ABSTRACT

This document discusses, among other things, methods and systems for facilitating automated device programming at changeout. A method comprises receiving, from a first device, physiological data at a temporary storage device; and processing the received physiological data, wherein the processing includes determining if a first signal processing function was used by the first device and substantially offsetting the first signal processing function if the first signal processing function was used by the first device; and processing the resultant physiological data to be compatible with a second device. The method further comprising providing the processed resultant physiological data to the second device.

20 Claims, 8 Drawing Sheets

(56) References Cited

OTHER PUBLICATIONS

"U.S. Appl. No. 12/839,913, Notice of Allowance mailed May 24, 2012", 8 pgs.

"U.S. Appl. No. 12/839,913, Response filed Mar. 2, 2012 to Non Final Office Action mailed Nov. 7, 2011", 8 pgs.

Rothbaum, Noah, "We've got your numbers.(cell phone address book system)", O, The Oprah Magazine, (Nov. 2005), 2 pgs.

Stern, et al., "Communication Systems Analysis and Design", Pearson Education ,Inc., (2004), pp. 232-234.

AUTOMATED DEVICE PROGRAMMING AT CHANGEOUT

CROSS-REFERENCE TO RELATED APPLICATIONS

This application is a Continuation of U.S. application Ser. No. 12/839,913, filed on Jul. 20, 2010, which is a Divisional of U.S. application Ser. No. 11/427,407, filed on Jun. 29, 2006, now issued as U.S. Pat. No. 7,783,356, the benefit of priority of each of which is claimed herein, and which is incorporated herein by reference in its respective entirety.

TECHNICAL FIELD

This patent document pertains generally to implantable medical devices, and more particularly, but not by way of limitation, to automated device programming at changeout.

BACKGROUND

Implantable medical devices (IMDs), including cardiac rhythm management devices such as pacemakers, implantable cardioverter defibrillators, and cardiac resynchronization therapy devices, typically have the capability to communicate data with an external device, such as an external programmer, via a telemetry link. While an external programmer is typically provided to program and modify the operating parameters of an IMD, modern IMDs also include the capability for bidirectional communication so that information, such as physiological data, can be transmitted to the programmer.

A typical expected lifespan of an implanted medical device may range from months to years. When an IMD reaches the end of its lifespan or when other events occur, such as a malfunction or defect that renders an IMD incapable of performing properly, the IMD is explanted and, in some cases, a new IMD is implanted to continue patient therapy.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
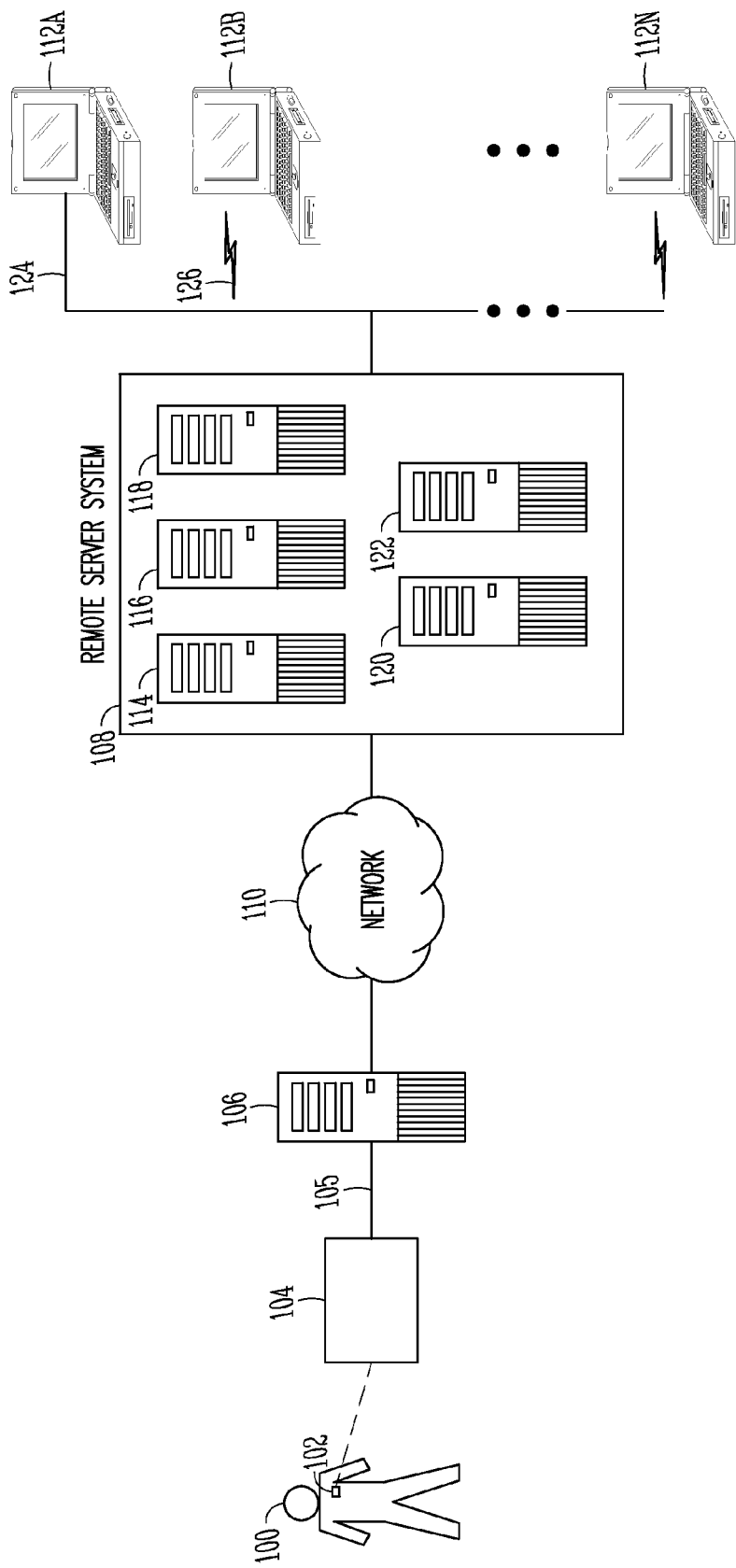
FIG. 1 is a schematic view illustrating portions of a system that enables physician-patient communication.

FIG. 1 is a schematic view illustrating portions of a system that enables physician-patient communication. In the example of FIG. 1, a patient 100 is provided with an implantable medical device (IMD) 102. Examples of implantable medical devices include a pacemaker, an implantable cardioverter defibrillator (ICD), a cardiac resynchronization therapy pacemaker (CRT-P), a cardiac resynchronization therapy defibrillator (CRT-D), a neurostimulation device, a deep brain stimulation device, a cochlear implant or a retinal implant. In some examples, the IMD 102 is capable of sensing physiological data and storing such data for later communication. Examples of physiological data include implantable electrograms, surface electrocardiograms, heart rate intervals (e.g., AA, VV, AV or VA intervals), electrogram templates for tachy discrimination, pressure (e.g., intracardiac or systemic pressure), oxygen saturation, activity, heart rate variability, heart sounds, impedance, respiration, intrinsic amplitude, or the like. The IMD 102 is capable of bidirectional communication with an external transceiver 104. In various examples, the IMD 102 receives commands from the transceiver 104 and may also communicate one or more patient indications to the transceiver 104. Patient indications may include such things as heart rate, heart rate variability, data related to tachyarrhythmia episodes, hemodynamic stability, activity, therapy history, autonomic balance motor trends, electrogram templates for tachy discrimination, heart rate variability trends or templates, or trends, templates, or abstractions derived from sensed physiological data. In another example, the IMD 102 may also communicate one or more device indications to the transceiver 104. Examples of device indications include lead/shock impedance, pacing amplitudes, pacing thresholds, or other device metrics. In other examples, the IMD 102 may communicate sensed physiological signal data to the transceiver 104, which may then communicate the signal data to a remote device for processing. Typically, the transceiver 104 is located in close proximity to the patient 100. The transceiver 104 may be included within or attached to a personal computer or a specialized device, such as a medical device programmer. In one example, the transceiver 104 is a hand-held device that is capable of connecting to a local computer 106. Typically, a connection 105 can be made using a hard-wired connection (e.g., serial, USB, Firewire) or a wireless connection (e.g., RF, IR). In some examples, the local computer 106 is a specialized device or a personal computer. In certain examples, the local computer 106 is adapted to communicate with a remote server system 108. The communication link between the local computer 106 and the remote server system 108 is typically made through a computer or telecommunications network 110. The network 110 may include, in various examples, wired and wireless networking such as the Internet, satellite telemetry, cellular telemetry, microwave telemetry, or other long-range communication networks. In some examples, the remote server system 108 comprises one or more computers, such as a database server 114, a network server 116, a file server 118, an application server 120 and a web server 122. In certain examples, one or more terminals 112A, 112B, . . . , 112N are connected to the remote server system 108. The terminals 112 are communicatively coupled to the remote server system 108 using a wired 124 or a wireless connection 126.

In some examples, the IMD 102 is adapted to store patient data and use the data to provide tailored therapy. For example, using historical physiological data, an IMD 102 may be able to discriminate between lethal and non-lethal heart rhythms and deliver an appropriate therapy. However, it is often desirable to establish a proper baseline of historical data by collecting a sufficient amount of data in the IMD 102. In some examples, a "learning period" of some time (e.g., thirty days) is used to establish the baseline for one or more physiological signals. An IMD 102 may, in an example, store a moving window of data of operation, such as a time period equal to the learning period, and use the information as a baseline indication of the patient's biorhythms or biological events.

When an IMD 102 malfunctions or reaches the end of its lifecycle, a new IMD (not shown) may be implanted in place of the retired IMD 102. In some examples, the replacement IMD is a newer or different model than the unit being replaced. In other examples, the replacement IMD is substantially the same as the explanted IMD. The replacement IMD, however, generally does not have the benefit of the historical patient data, and thus, the patient 100 must endure another learning period as the new IMD builds its baseline. In addition, any patient-specific device settings stored on the explanted IMD 102 are typically not automatically transferred to the replacement device. The current inventor has recognized that providing historical patient data to a replacement IMD advantageously bypasses any necessary learning period. Additionally, the current inventor has recognized that automatically transferring device settings to a replacement IMD may be more efficient and less prone to human error.

Figure 2:
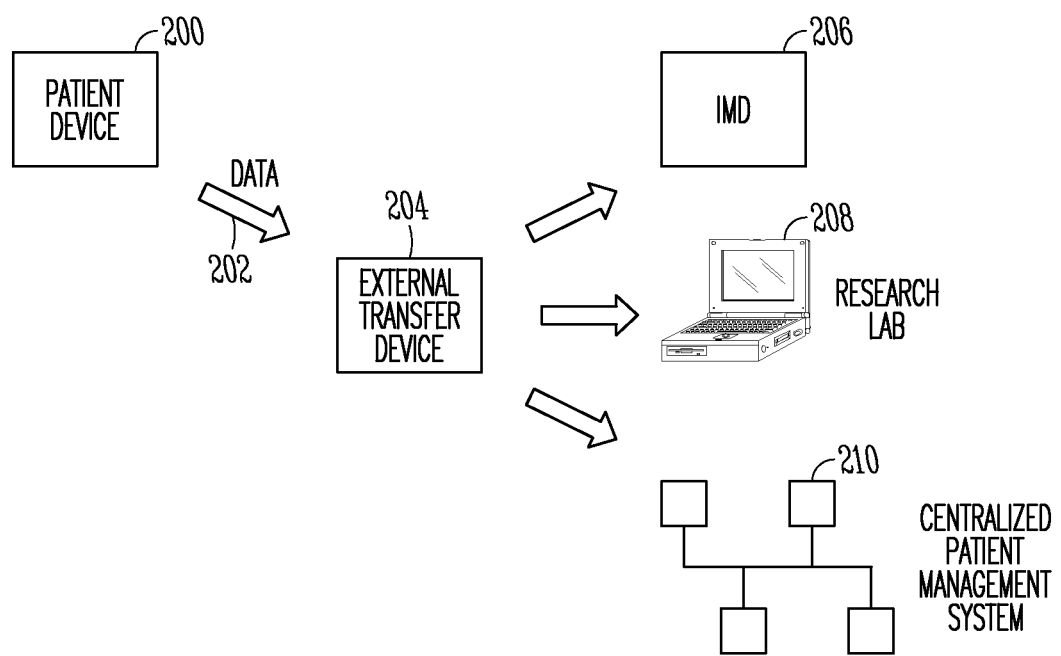
FIG. 2 is a dataflow diagram illustrating portions of a system capable of automatic data transfer.

FIG. 2 is a dataflow diagram illustrating portions of a system capable of automatic data transfer. A first patient device 200 is capable of sensing a patient's physiological data and storing such data. In an example, the first patient device 200 includes an IMD, such as one illustrated in FIG. 1 at 102. In other examples, the first patient device 200 may be an external patient monitoring device, such as an electrocardiograph machine, Holter monitor, blood pressure cuff, pulse oximeter, posture sensor, accelerometer, EEG monitor or respiration monitor. Data 202 stored on the first patient device 200 is transferred to the external transfer device 204. In some examples, the data transfer is enabled by wireless communication, such as inductive telemetry or radio frequency telemetry. In another example, the data transfer is performed over a wired communication link, such as a serial connection.

Data 202 may include stored physiological data, calculated summary data, event data or device data. For example, an implantable medical device may sense and collect raw physiological data, temporarily store the physiological data, use the data to calculate summary data, such as trend data, and store the trend data while discarding the temporarily stored raw physiological data. By only storing summary data, such as trend data, a more efficient use of the device's internal memory may be achieved. As another example, when an implanted medical device senses an event, such as a tachyarrhythmia episode, the IMD may store event markers or other details about the event (e.g., time of event, severity, length of event). Historical event data can be used for predictively determining similar future events and adapting treatment accordingly.

In an example, the external transfer device 204 can temporarily store the data 202 and process the stored data 202. For example, if the first patient device 200 is an IMD that is being explanted to be replaced with another IMD 206, the external transfer device 204 may condition the data 202 to be compatible with the replacement IMD 206. The conditioning may, in some examples, not involve any data transformation, such as when the first patient device 200 and the IMD 206 are substantially the same device. In other examples, the data conditioning may involve complex de-filtering and re-filtering of data, such as when the replacement IMD 206 is a different model or has different capabilities than the first patient device 200. In another example, the conditioning may only partially transform the data, such as to an un-processed or raw, sensed form, and provide the data to the target device (e.g., the replacement IMD 206), which can treat it as sensed data and perform its own signal processing. In addition, data conditioning may involve a translation of device settings, such as from one device model to another model with more or fewer settings, or with settings that may be a combination or sub-combination of the other device's settings.

As another example, the external transfer device 204 may also provide data 202, either processed or unprocessed, to another destination, such as a research laboratory 208 or a centralized patient management system 210. Users at a research laboratory 208 may be interested in the data 202 for several reasons including offline analysis or simulation. In addition, providing data 202 to a centralized patient management system 210 may allow for other health care practitioners to access the data for research, statistical population use, patient monitoring, or for data recovery purposes. In other examples, the external transfer device 204 may also provide data 202, either processed or unprocessed, to an external patient monitor (not shown) or a data storage device (not shown).

Figure 3:
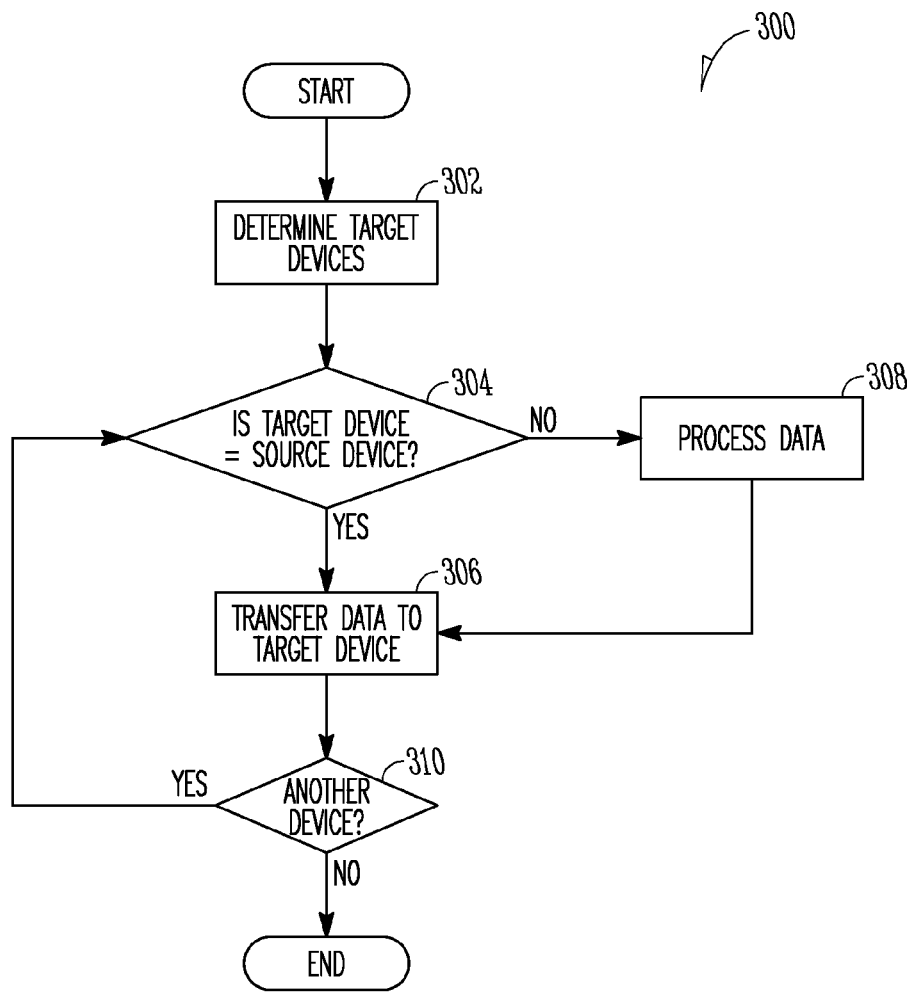
FIG. 3 is a flowchart illustrating a method for transferring data.

FIG. 3 is a flowchart illustrating a method 300 for transferring data. At 302, one or more target devices are determined. Examples of target devices may include an external patient monitor, an implantable medical device, or a data storage device (e.g., a database associated with a research laboratory or a centralized patient management system). At 304, the method 300 determines if the target device is the substantially the same as the source device. For example, if a source device, such as an IMD, malfunctions or is defective, a same or similar device may be used to replace the defective unit. The replacement device may have many, if not all, of the same signal processing or other capabilities and features. As such, no data transformation is needed and at 306, the data can be transferred to the target device with little or no data processing. However, if the target device is different, such as may be the case when an IMD is upgraded or if the data is transmitted to an external system for other uses, depending on the data transmitted, certain processing may be needed to transform the data into a form compatible with the target device.

At 308, the data is processed. In an example, at 308 the data is processed to a format compatible with the target device before being transferred (block 306). In another example, the data is processed to a substantially unprocessed (e.g., sensed) format at 308. Then the substantially unprocessed data is transferred to the target device (block 306) where the data is processed by the target device, such that it is substantially similar to the target device's native format. At 310, the method 300 determines if the data is to be transferred to another device. If so, then the method 300 proceeds to decision block 304 to continue processing.

Figure 4:
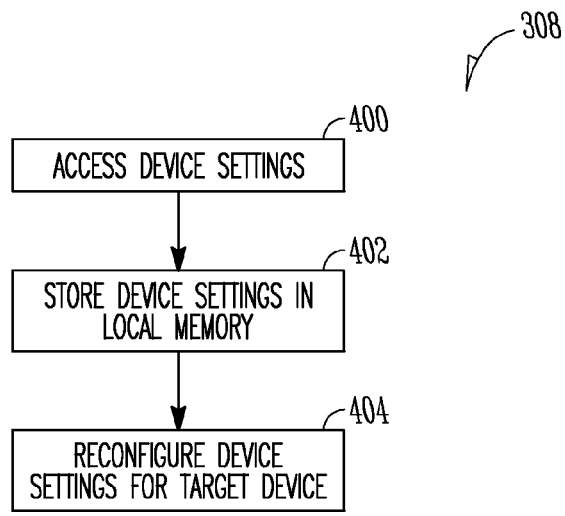
FIGS. 4-7 are flowcharts illustrating a method for processing data for transfer to a target device.

FIG. 4 is a flowchart illustrating a method 308 for processing data for transfer to a target device. At 400, the method 308 accesses a source device's device settings. Device settings may include such things as a tachy rate zone, a brady pacing mode, one or more thresholds of tachy discrimination algorithms, a tachy therapy parameter, a morphological template, a brady therapy parameter, one or more thresholds of heart failure decompensation detection algorithms, one or more thresholds of apnea detection algorithms, a patient name, a patient gender, a patient birth date, a patient height, a patient weight, a patient New York Heart Association class, a patient left ventricular ejection fraction, a physician contact information or other settings, preferences, options, or threshold values that may be stored on a device to control its operation. At 402, the source device settings are stored in local memory in an intermediary transfer device. At 404, the source device settings are reconfigured, if necessary, to be compatible with a target device.

Figure 5:
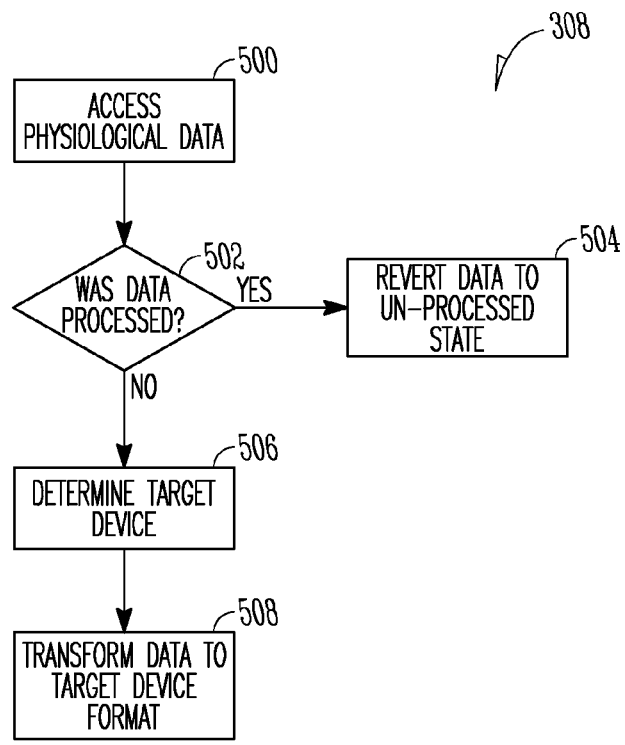

FIG. 5 is a flowchart illustrating a method 308 for processing data for transfer to a target device. At 500, the method 308 accesses physiological data. In an example, the physiological data is provided directly by the source device. In another example, the physiological data is accessed from a storage device, such as a memory stick or a hard drive, which contains some of all of the physiological data collected by the source device.

At 502, the method 308 determines if the data was processed by the source device. In an example, a lookup table is used to record and track which signals are modified or processed on which devices in which modes. Also, an indication of how the signals were modified or processed is recorded in the lookup table for later reference when determining how to invert or revert such processing. For example, the source device may collect raw signal data and then process it, such as with a signal processing function, and only store the processed signal data. Signal processing functions may include a frequency-selective function, an upsampling function, a downsampling function, a re-sampling function, a filtering function, an amplifying function, an attenuating function, an averaging function, a function to calculate the median, mode, standard deviation or quartiles, a function to build a histogram, a function to estimate a probability distribution function or cumulative distribution function or a compressing function in various examples. Alternatively, the source device may store the raw or lesser-processed sensed signal data either alone or in combination with more-processed data. In an example, if both a lesser-processed signal data set and a more-processed signal data set are available, the method 308 can attempt to de-process the lesser-processed signal data first. This may advantageously avoid introducing artifacts when trying to reverse the additional processing undergone by the more-processed signal data set.

At 504, if the signal data was initially processed by the source device, then the data is at least partially de-processed, such as to substantially revert to the original signal data format. For example, a source IMD may sense electrocardiogram data and use a first filter function $H_1$ to filter the incoming signal to remove noise and provide a cleaner signal to analyze. In order to de-process or substantially revert the data toward the original signal form, the method 308 may apply an inverse filter function $H^{-1'}_1$, where "'" indicates that $H^{-1'}_1$ is an estimate of an inverse function of $H_1$, as an exact inverse function may not be possible due to mathematical limitations or limitations of physics. In some examples, the first filter function $H_1$ is a linear determined 1:1 process and thus, an actual inverse filter function $H^{-1}_1$ can be realized and implemented such that $H^{-1'}_1 = H^{-1}_1$ and the resulting signal has no distortion. In examples, the inverse filter function $H^{-1}_1$ is applied in a time domain or a frequency domain. In a further example, the inverse filter function $H^{-1'}_1$ includes an amplitude-modification function. For example, a first IMD may provide 8-bit data storage whereas a second IMD may provide 12-bit data storage. To properly transform binary data from the first IMD's format to the second IMD's format, a left shift of 4 bits is used, which will appropriately scale the binary data to the second IMD's native format. As another example, if an input signal was subjected to automatic gain control or intentional gain compression (e.g., non-linear gain) at a first IMD, to compensate, one or more functions may be used to reverse the first IMD's transfer function to produce substantially unprocessed data.

In a further example, either the actual inverse filter function $H^{-1}_1$ or the estimated inverse filter function $H^{-1'}_1$ may be determined based on population data of patients with the same or similar devices, or with devices that implement the same acquisition filter function $H_1$. In such an example, the inverse filter function (e.g., $H^{-1}_1$, $H^{-1'}_1$) can be approximated using methods such as adaptive filtering or using a neural network, which seek to minimize signal distortion until, for example, the distortion meets a "minimum distortion" criteria or threshold. In general, a population-based derivation method may be helpful in the cases where it is difficult or computationally expensive to directly derive $H^{-1}_1$ from $H_1$ or when a derivation results in unacceptable distortion.

In an example, the inverse filter function $H^{-1'}_1$ is designed such that a comparison between the reconstructed signal and the original raw signal indicate minimal distortion. For example, the inverse filter function $H^{-1'}_1$ is designed to minimize one or more of a mean squared error, a minimum phase shift, a minimum dominant frequency component deterioration, a reserved signal-to-noise ratio, or a high cross-correlation between the raw and the reconstructed signal data.

Similarly, if multiple signal processing functions were used during data acquisition, then one or more other signal processing functions can be reversed by applying one or more other corresponding inverse or reverse signal processing functions.

Using either an analytical or a data-driven (e.g., population-based) method a maximum error or distortion in signal magnitude or phase introduced by $H^{-1'}_1$ can be determined. The maximum error may be used to indicate quantitatively how good the estimate $H^{-1'}_1$ is. Using the quantitative value as an "error bound" of the reconstructed signal, the rate of false detection (due to magnitude distortion) and/or the timing error of the detected event (due to phase distortion) may be determined and used to adjust discrimination processes when detecting an event.

At 506, a target device is determined. The target device may include a second (replacement) IMD, a workstation in a research computer system or a database in a centralized patient management system. In addition, the target device may be an offline storage device or a simulation or analysis machine.

At 508, the physiological data is transformed to the target device's format. For example, the target may be an IMD that uses its own signal processing function $H_2$. In order to transform the physiological data obtained from the source IMD to simulate data captured on the target IMD, an associated function $H'_2$ can be used. Again, the "'" indicates that $H'_2$ is an estimate of $H_2$, as it may not be possible to recreate $H_2$ exactly due to mathematical limitations or limitations of physics. In some examples, $H_2=H'_2$, such that the function used to transform or make the data compatible with the target device is the same as that used by the target device during its own data acquisition process. In other examples, a different function or group of functions may be used to prepare the data for the target device.

Figure 6:
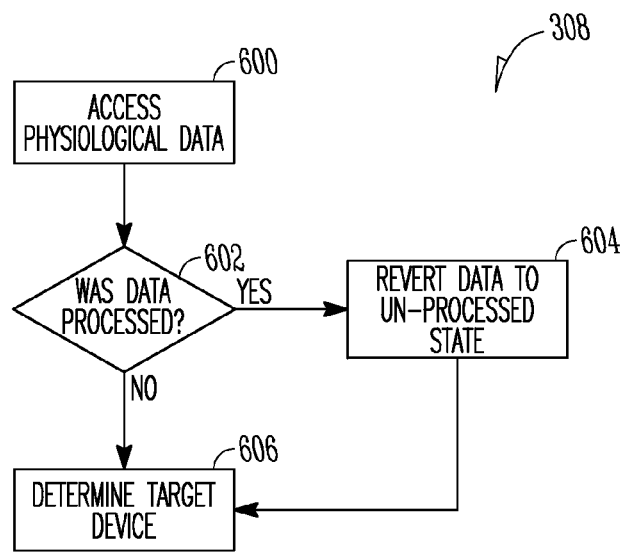

FIG. 6 is a flowchart illustrating a method 308 for processing data for transfer to a target device. At 600, the method 308 accesses physiological data. At 602, the method 308 determines if the data was processed by the source device. Processes and methods used to access and determine if the data was processed by the source device are substantially similar to those described above (500 and 502 in FIG. 5).

At 604, if the signal data was initially processed by the source device, then the data is at least partially de-processed, such as to substantially revert to the original signal data format. For example, a source IMD may sense electrocardiogram data and use a first filter function $H_1$ to filter the incoming signal to remove noise and provide a cleaner signal to analyze. In order to de-process or substantially revert the data toward the original signal form, the method 308 may apply an inverse filter function $H^{-1}{}'_1$, where "'" indicates that $H^{-1}{}'_1$ is an estimate of an inverse function of $H_1$, as an exact inverse function may not be possible due to mathematical limitations or limitations of physics. As described above with reference to FIG. 5, the inverse filter function $H^{-1}{}'_1$ may appear in one or more forms, such as an actual inverse filter function $H^{-1}{}_1$, applied in a time domain or a frequency domain, implemented as an amplitude-modification function, determined with population data or a neural network, or designed to minimize distortion using one or more error metrics. Similarly, if multiple signal processing functions were used during data acquisition, then one or more other signal processing functions can be reversed by applying one or more other corresponding inverse or reverse signal processing functions.

At 606, a target device is determined. The target device may include a second (replacement) IMD, a workstation in a research computer system or a database in a centralized patient management system. In addition, the target device may be an offline storage device or a simulation or analysis machine. In an example, the reverted (e.g., substantially unprocessed) data is provided to the determined target device, which may use its native signal processing functions to process the data.

Figure 7:
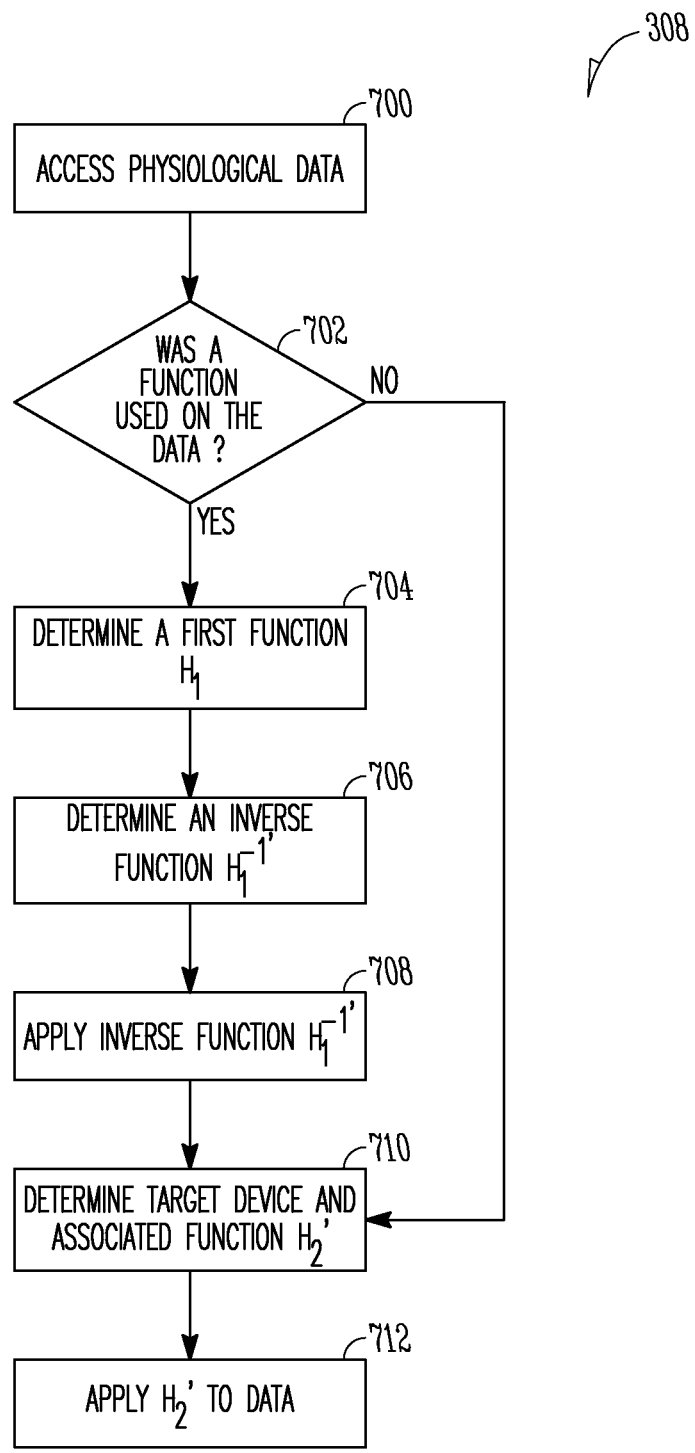

FIG. 7 is a flowchart illustrating a method 308 for processing data for transfer to a target device. At 700, the method 308 access physiological data associated with a source device. In one example, the source device may collect physiological data and store it in internal memory. In another example, the source device may only store a portion of the collected data and transfer other data to a separate device. For example, a source device (e.g., an IMD) may store a moving window of data and at periodic intervals (e.g., daily) transfer the oldest data out of storage to make room for the next day's data acquisition. The source device may, for instance, transfer the historical data to a local storage device (e.g., a personal computer) or a networked storage device (e.g., a network database) for archival storage.

At 702, the method 308 determines if the physiological data was modified during acquisition by a first signal processing function. In some examples, as the physiological data is acquired at a source device, the first signal processing function includes a first filter to clean and prepare the data for analysis. If the physiological data was modified by signal processing by the source device, then the method 308 determines the function that was used.

In an example, more than one function may be used to process acquired data at the source device. In some examples, the functions may be applied serially. For example, the source device may sample, buffer, amplify, filter, upsample, downsample, or perform analog-to-digital conversion on an intrinsic cardiac signal. In other examples, one or more functions may be applied at different times during signal acquisition.

Figure 8:
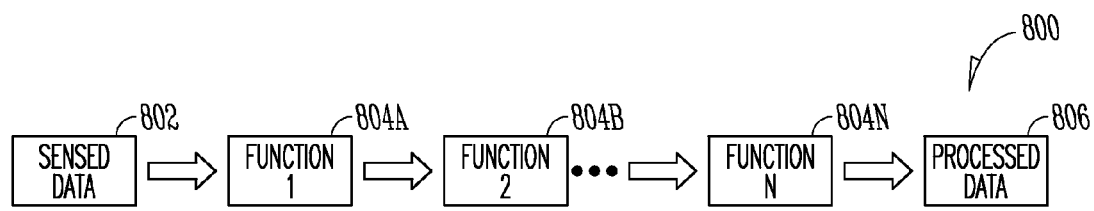
FIG. 8 is a diagram illustrating an implementation using multiple functions in serial on acquired data.

FIG. 8 is a diagram illustrating an implementation using multiple functions in serial on acquired data. In the dataflow diagram 800, sensed data 802 is acquired and stored in the source device. A first function 804A is applied to the data, followed by one or more additional functions 804B ... 804N, where the result is processed data 806, which may be stored and used by the source device during its operation.

Figure 9:
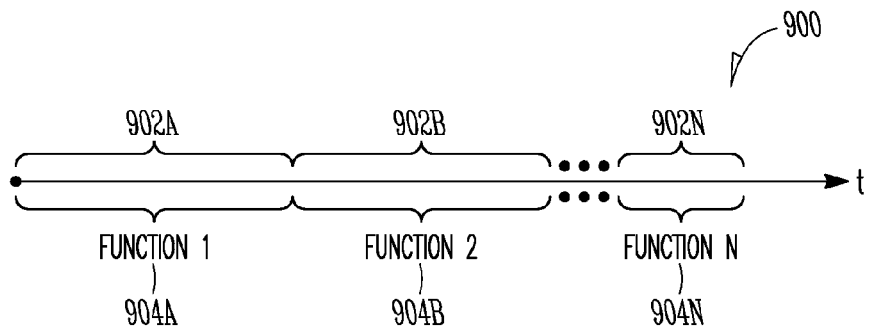
FIG. 9 is a diagram illustrating an implementation using multiple functions varying over time on acquired data.

FIG. 9 is a diagram illustrating an implementation using multiple functions varying over time on acquired data. In the timeline diagram 900, data captured by the source device during a first time period 902A is processed by a first function 904A. As time progresses, at a second time period 902B, a second function 904B is used, and at an Nth time period 902N, an Nth function 904N is used. Such different functions may result, for example, from applying different programmable filter constants during different time periods. In certain examples, a log of the device's history of filter constants or other programmable signal processing parameters is stored by the device. The log may be accessed, such as during transfer, so that the appropriate de-processing function can be applied to the physiological signal over time periods when different signal processing functions were used.

Referring to FIG. 7 again, at 704, if the data was processed, then a first signal processing function $H_1$ is determined.

At 706, an inverse signal processing function $H^{-1}{}'_1$ is determined. As discussed above, $H^{-1}{}'_1$ may be an actual inverse function or an estimated inverse function conforming to a minimum threshold level of distortion. In some examples, the inverse function may be a multi-step process, such as involving multiple sequential functions to substantially reverse the processing effects of the source device's acquisition process. In an example, when multiple sequential functions were used during the data acquisition, a reverse sequence of corresponding inverse functions is determined.

At 708, the inverse function $H^{-1}{}'_1$ is applied to the physiological data. In an example, more than one inverse function is needed to revert the data to its raw form. For example, if the source device applied three filter functions in series to the raw sensed data, the temporary device would use one or more corresponding inverse filter functions to undo the processing. Similarly, if the source device's acquisition processing involved first filtering and then down-sampling, then the temporary device's recovery processing may involve first up-sampling and then inverse-filtering.

At 710, a target device and an associated signal processing function $H'_2$ are determined. For example, if the target device is a replacement IMD, a function $H'_2$ is determined such that the function will transform the reverted physiological data to a form that is substantially similar to that of the target device's signal-processed format.

As described above, in order to transform the physiological data obtained from the source IMD to simulate data captured on the target IMD, an associated function $H'_2$ can be used. The "'" indicates that $H'_2$ is an estimate of $H_2$, as it may not be possible to recreate $H_2$ exactly due to mathematical limitations or limitations of physics. In some examples, $H_2 = H'_2$, such that the function used to transform or make the data compatible with the target device is the same as that used by the target device during its own data acquisition process. In other examples, a different function or set of functions may be used to prepare the data for the target device.

At 712, the transformation function $H'_2$ is applied to the reverted physiological data. In an example, more than one filter function is used to transform the data to a compatible form.

Figure 10:
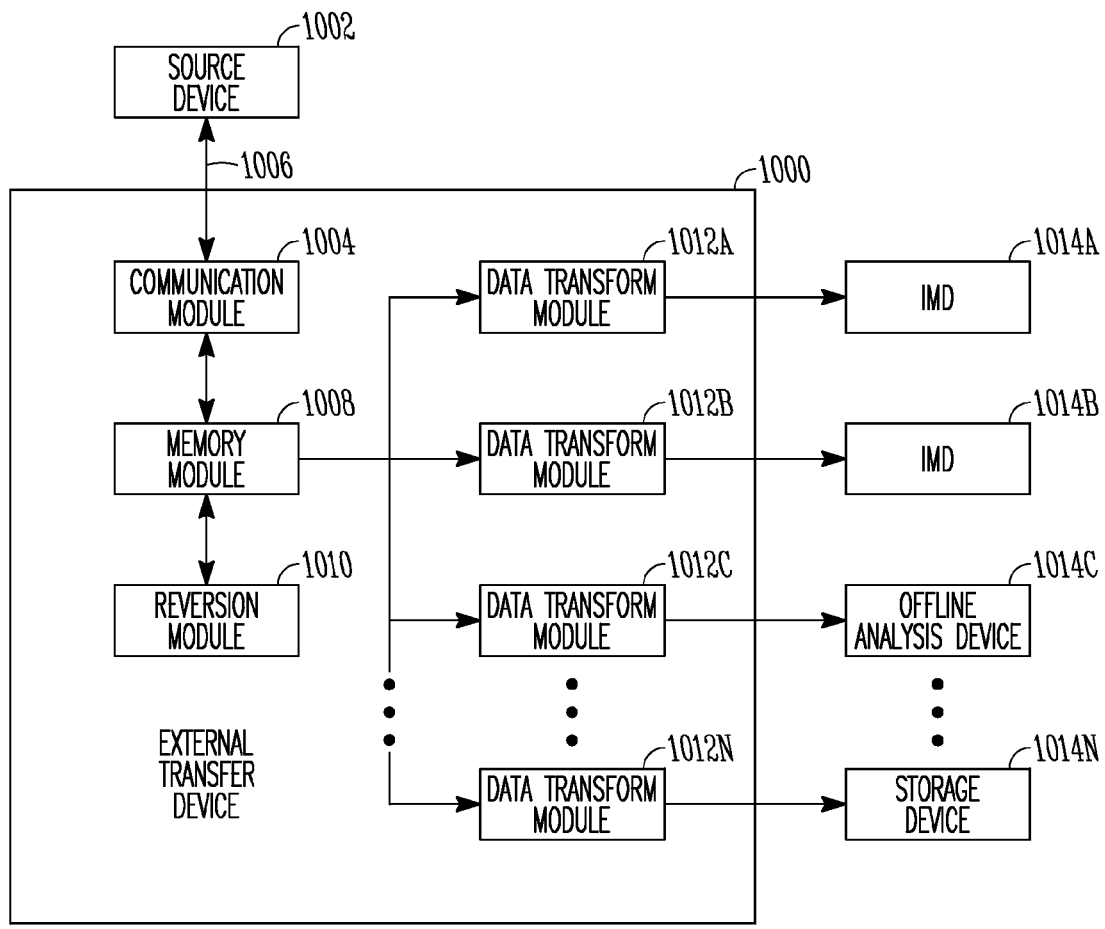
FIG. 10 is a schematic diagram illustrating an external transfer device capable of transforming data and transferring the transformed data to another device.

FIG. 10 is a schematic diagram illustrating an external transfer device 1000 capable of transforming data and transferring the transformed data to another device. In FIG. 10, a communication module 1004 accesses physiological data on a source device 1002. The communication module 1004 may communicate with the source device 1002 via a wired or wireless communication link 1006. Examples of wired communication may include serial or parallel cabled communication. Examples of wireless communication may include inductive telemetry, short-range or long-range radio frequency telemetry, or infrared telemetry. Physiological data transferred from the source device 1002 is stored in a memory module 1008. Memory module 1008 may include flash memory, random access memory, hard drive storage, optical drive storage, or other computerized storage mechanisms. A reversion module 1010 accesses the stored physiological data from the memory module 1008 and de-processes the data, such that the de-processed data is substantially in the same form as original sensed data. The reversion module 1010 may store the resultant data in the memory module 1008. The external transfer device 1000 may include one or more data transform modules 1012A, 1012B, 1012C, . . . , 1012N. Each data transform module 1012 may be tailored for use with one or more target devices 1014A, 1014B, 1014C, . . . , 1014N. A data transform module 1012 can access the reverted physiological data in the memory module 1008, transform the physiological data to a compatible form for a particular type of target device, and provide the resulting compatible data to a target device 1014 of that particular type.

Figure 11:
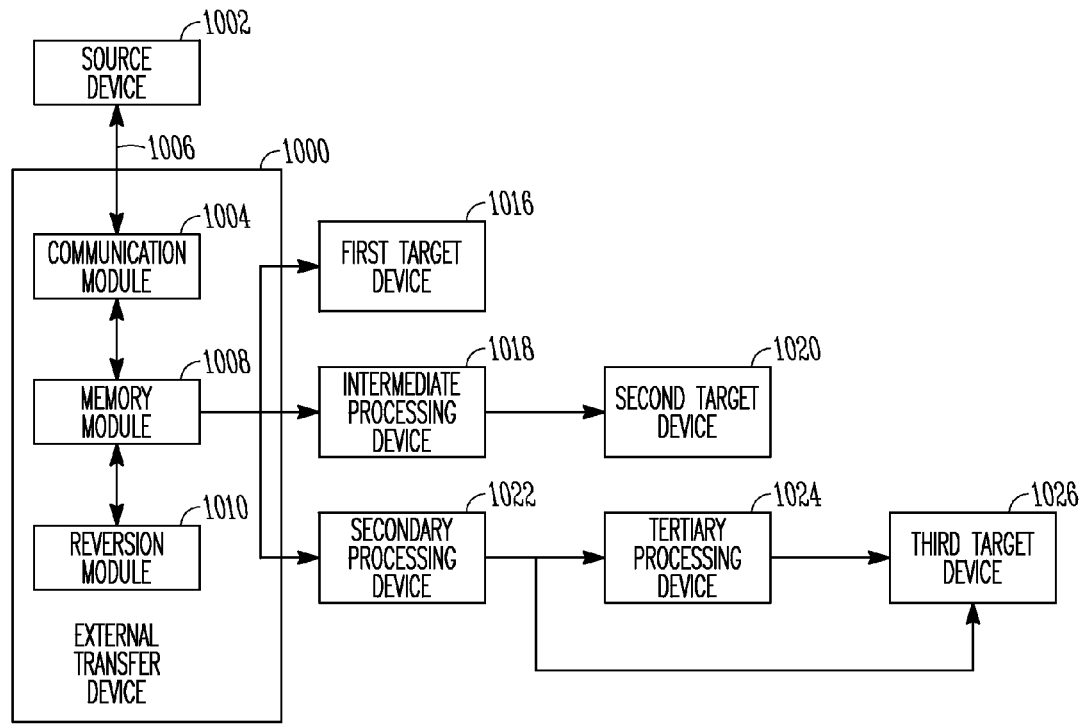
FIG. 11 is a schematic diagram illustrating another example of an external transfer device capable of transforming data and transferring the transformed data to another device.

FIG. 11 is a schematic diagram illustrating another example of an external transfer device 1000 capable of transforming data and transferring the transformed data to another device. Some or all of the functionality described in the example illustrated in FIG. 11 may exist in the example illustrated in FIG. 10. In some examples, the external transfer device 1000 may partially or fully de-process physiological data using the reversion module 1010. De-processed data can be provided to a first target device 1016, which can then transform the physiological data to a compatible form. In an example, the first target device 1016 is an IMD and de-processed signal data is processed in a similar manner as sensed physiological data using the first target device's native signal processing function.

De-processed data can also be provided to one or more intermediate processing devices 1018. The intermediate processing devices 1018 can then transform the physiological data to be compatible with a second target device 1020. The intermediate processing devices 1018 may process the de-processed data serially or in parallel. After fully transforming the data, the re-processed physiological data is transferred to the second target device 1020.

In some cases, de-processing is a multi-step process and the external transfer device 1000 can perform one or more steps and transfer the partially de-processed data to a secondary processing device 1022, which can complete the de-processing. In other examples, two or more secondary processing devices (not shown) can be used, either serially or in parallel, to further process the partially de-processed data received from the external transfer device 1000. Fully de-processed data can then be transferred to one or more tertiary processing devices 1024. The tertiary processing devices 1024 can re-process the physiological data such that it is compatible with a third target device 1026. Alternatively, the third target device 1026 can receive the de-processed physiological data from the secondary processing device 1024 to process internally, such as with the same or similar signal processing function used during data acquisition.

Figure 12:
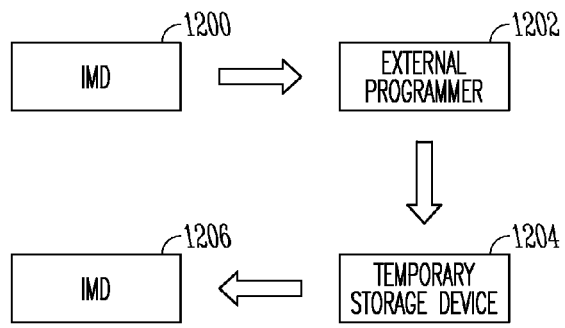
FIG. 12 is a schematic diagram illustrating another configuration to transfer and transform data from one device to another device.

FIG. 12 is a schematic diagram illustrating another configuration to transfer and transform data from one device to another device. A first IMD 1200 may communicate with an external programmer 1202 and transmit physiological data, such as in the form of processed or unprocessed signal data. The external programmer 1202 may process the data. However, in some examples, a temporary storage device 1204 is used to process the data (e.g., de-process the data to a substantially unprocessed form and then process the data to be compatible with the target device) and the external programmer 1202 merely acts as a conduit between the first IMD 1200 and the temporary storage device 1204. The temporary storage device may include, in some examples, a memory stick (e.g., a flash memory device). In an example, the temporary storage device 1204 connects with a second IMD 1206 to transfer the transformed data to the second IMD 1206.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

For the purposes of this specification, the term "machine-readable medium" or "computer-readable medium" shall be taken to include any medium which is capable of storing or encoding a sequence of instructions for execution by the machine and that cause the machine to perform any one of the methodologies of the inventive subject matter. The terms "machine-readable medium" or "computer-readable medium" shall accordingly be taken to include, but not be limited to, solid-state memories, optical and magnetic disks, and carrier wave signals. Further, it will be appreciated that the software could be distributed across multiple machines or storage media, which may include the machine-readable medium.

Method embodiments described herein may be computer-implemented. Some embodiments may include computer-readable media encoded with a computer program (e.g., software), which includes instructions operable to cause an electronic device to perform methods of various embodiments. A software implementation (or computer-implemented method) may include microcode, assembly language code, or a higher-level language code, which further may include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The foregoing description of specific embodiments reveals the general nature of the inventive subject matter sufficiently that others can, by applying current knowledge, readily modify and/or adapt it for various applications without departing from the generic concept. Therefore, such adaptations and modifications are within the meaning and range of equivalents of the disclosed embodiments. The phraseology or terminology employed herein is for the purpose of description and not of limitation. Accordingly, the inventive subject matter embraces all such alternatives, modifications, equivalents and variations as fall within the spirit and broad scope of the appended claims.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A system comprising:
an ambulatory medical device, comprising:
  a communications port, adapted to receive reverted physiological data from an external processing device;
  a memory, to store the received reverted physiological data; and
  a processor, to process the received reverted physiological data by applying a third signal processing function to convert the received reverted physiological data to be compatible with a process executed on the ambulatory medical device,
  wherein the reverted physiological data was produced by the external processing device by:
    receiving physiological data from a first medical device, wherein the physiological data was obtained from raw data by the first medical device using a first signal processing function;
    processing the received physiological data by applying a second signal processing function to the received physiological data, wherein the second signal processing function substantially reverses the first signal processing function to provide the reverted physiological data, and wherein the reverted physiological data is approximate to the raw data; and
    transmitting the reverted physiological data to the ambulatory medical device using a modulation signal processing function; and
  wherein the ambulatory medical device is further adapted to receive the reverted physiological data using a demodulation signal processing function.

2. The system of claim 1, wherein the external processing device includes an external programmer for an implantable medical device, and wherein at least one of the first medical device and the ambulatory medical device is an implantable medical device.

3. The system of claim 1, wherein the communications port is adapted to be connected to an external programmer, and wherein the first medical device is an ambulatory medical device.

4. The system of claim 1, wherein the ambulatory medical device is an implantable medical device.

5. The system of claim 1, wherein the communications port includes a USB connector.

6. The system of claim 1, wherein the reverted physiological data includes electrocardiogram data.

7. The system of claim 1, wherein the reverted physiological data is associated with a tachyarrhythmia episode.

8. The system of claim 1, wherein the second signal processing function is calculated to minimize at least one of a mean squared error, a minimum phase shift, a minimum dominant frequency component deterioration, a reserved signal-to-noise ratio, or a high cross-correlation between sensed physiological data and the resultant physiological data.

9. The system of claim 1, wherein at least one of the first and second signal processing functions include at least one of a frequency-selective function, an upsampling function, a downsampling function, a re-sampling function, a filtering function, an amplifying function, an attenuating function, an averaging function, a function to calculate the median, mode, standard deviation or quartiles, a function to build a histogram, a function to estimate a probability distribution function or cumulative distribution function, or a compressing function.

10. The system of claim 1, wherein the external processing device is adapted to apply the second signal processing function in a time domain.

11. The system of claim 1, wherein the external processing device is adapted to apply the second signal processing function in a frequency domain.

12. The system of claim 1, wherein the second signal processing function comprises a plurality of signal processing functions aggregated to substantially reverse the effects of the first signal processing function on the raw data.

13. The system of claim 1, wherein the external processing device is adapted to receive device settings associated with the first medical device, and wherein the external processing device is adapted to configure the device settings to be compatible with the ambulatory medical device.

14. The system of claim 13, wherein the ambulatory medical device is adapted to receive the device settings from the external processing device via the communications port and implement the device settings at the ambulatory medical device.

15. The system of claim 13, wherein the device settings include at least one of a tachy rate zone, a brady pacing mode, one or more thresholds of tachy discrimination algorithms, a tachy therapy parameter, a morphological template, a brady therapy parameter, one or more thresholds of heart failure decompensation detection algorithms, one or more thresholds of apnea detection algorithms, a patient name, a patient gender, a patient birth date, a patient height, a patient weight, a patient New York Heart Association class, a patient left ventricular ejection fraction, or a physician contact information.

16. A method comprising:
  receiving at an ambulatory medical device, reverted physiological data from an external processing device, wherein the reverted physiological data was produced by the external processing device by:
    receiving physiological data from a first medical device, wherein the physiological data was obtained from raw data by the first medical device using a first signal processing function; and
    processing the received physiological data by applying a second signal processing function to the received physiological data, wherein the second signal processing function substantially reverses the first signal processing function to provide the reverted physiological data, and wherein the reverted physiological data is approximate to the raw data;
    transmitting the reverted physiological data to the ambulatory medical device using a modulation signal processing function; and
  at the ambulatory medical device:
    receiving the reverted physiological data using a demodulation signal processing function;
    storing the received reverted physiological data; and
    processing the received reverted physiological data by applying a third signal processing function to convert the received reverted physiological data to be compatible with a process executed on the ambulatory medical device.

17. The method of claim 16, comprising:
  receiving device settings from the external processing device; and
  implementing the device settings at the ambulatory medical device;
  wherein the external processing device received device settings associated with the first medical device and configured the device settings to be compatible with the ambulatory medical device.

18. The method of claim 16, wherein the reverted physiological data includes electrocardiogram data.

19. The method of claim 16, wherein the reverted physiological data is associated with a tachyarrhythmia episode.

20. An ambulatory medical device, comprising:
  a communications port, adapted to receive reverted physiological data from an external processing device;
  a memory, to store the received reverted physiological data; and
  means for processing the received reverted physiological data to convert the received reverted physiological data to be compatible with a process executed on the ambulatory medical device,
  wherein the reverted physiological data was produced by the external processing device by:
    receiving physiological data from a first medical device, wherein the physiological data was obtained from raw data by the first medical device using a first signal processing function;
    processing the received physiological data by applying a second signal processing function to the received physiological data, wherein the second signal processing function substantially reverses the first signal processing function to provide the reverted physiological data, and wherein the reverted physiological data is approximate to the raw data; and
    transmitting the reverted physiological data to the ambulatory medical device using a modulation signal processing function; and
  wherein the ambulatory medical device is further adapted to receive the reverted physiological data using a demodulation signal processing function.

* * * * *